United States Patent [19]

Gaudion et al.

[11] Patent Number: 4,748,007

[45] Date of Patent: May 31, 1988

[54] ENDOSCOPE DISINFECTING AND STORING DEVICE

[75] Inventors: John R. Gaudion, Columbus; Phillip L. Gerwig, Ashland; Jeffrey J. Sopko, Brecksville, all of Ohio

[73] Assignee: Vetrodyne, Inc., Cleveland, Ohio

[21] Appl. No.: 802,593

[22] Filed: Nov. 27, 1985

[51] Int. Cl.$^4$ ............... A61L 2/18; B08B 9/00; B08B 11/02
[52] U.S. Cl. .................................. 422/300; 134/170
[58] Field of Search ..................... 422/292, 300; 134/22.11, 170, 199; 128/4

[56] References Cited

U.S. PATENT DOCUMENTS

| | | | |
|---|---|---|---|
| 3,488,141 | 1/1970 | Rausing | 422/300 |
| 3,963,438 | 6/1976 | Banez | 134/22.11 X |
| 4,064,886 | 12/1977 | Heckele | 134/171 X |
| 4,288,882 | 9/1981 | Takeuchi | 134/199 X |
| 4,496,522 | 1/1985 | McConnell | 134/22.11 X |

OTHER PUBLICATIONS

Exhibit A, KEY-MED, Bronchoscope Disinfection Stand Brochure.

Exhibit B, Medical Engineering Laboratory, Inc.—Medi-Board Brochure.

*Primary Examiner*—Barry S. Richman
*Assistant Examiner*—Jill Johnston
*Attorney, Agent, or Firm*—Pearne, Gordon, McCoy & Granger

[57] ABSTRACT

A device for disinfecting and storing endoscopes and the like includes a pair of vertically spaced, wall-mounted brackets between which extend a plurality of parallel connecting rods for supporting the brackets in fixed position relative to each other. A pair of vertically extending tubes for holding disinfecting liquid are locked in position between the brackets by a pair of annular cam-action nuts engaging the top ends of the tubes, the nuts being rotatable to release the tubes for removal and cleaning at a remote location. Elastomeric plugs inserted into the bottom ends of the tubes preclude leakage of disinfecting liquid therefrom. Alternatively, valve assemblies can be provided at the bottom ends of the tubes to permit drainage of the disinfecting liquid from the tubes when in their mounted positions. The uppermost bracket supports the annular nuts which in turn support one or two endoscopes with their insertion portions extending through the annular nuts into the disinfecting liquid within the tubes.

8 Claims, 5 Drawing Sheets

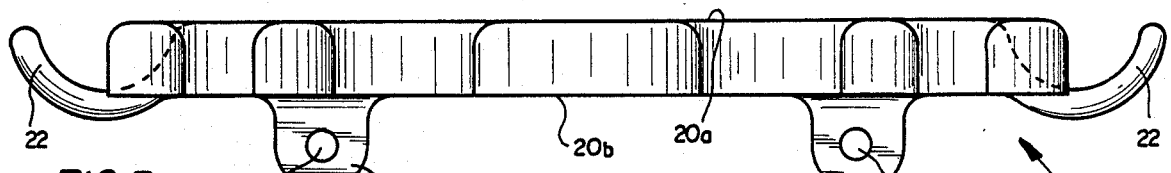
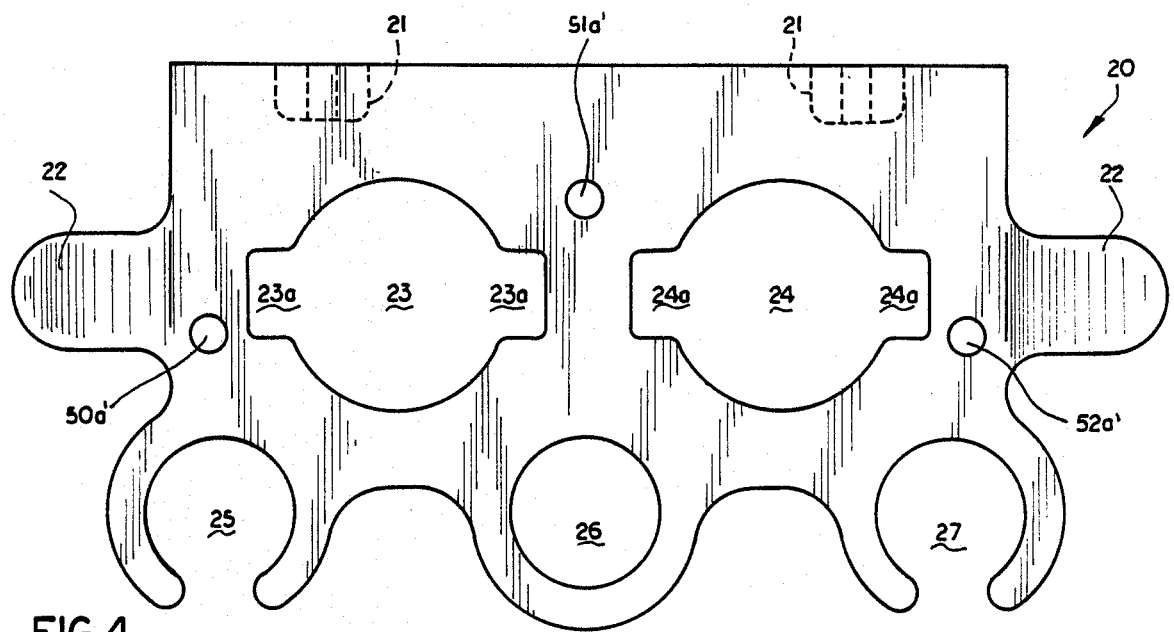
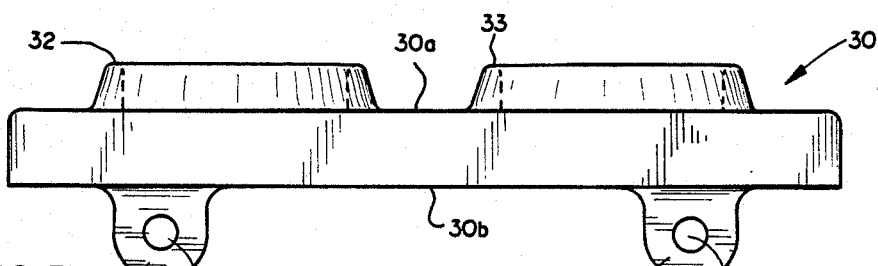
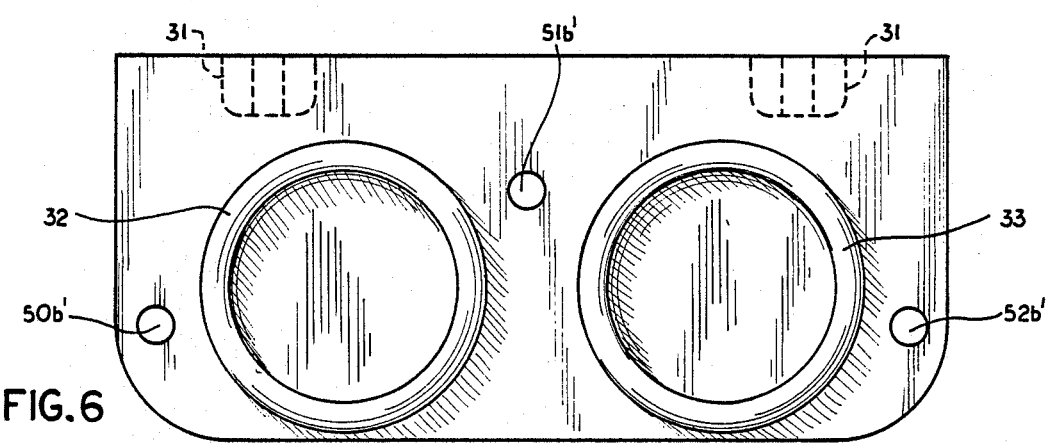

ENDOSCOPE DISINFECTING AND STORING DEVICE

BACKGROUND OF THE INVENTION

The present invention relates in general to devices for maintaining medical equipment, and more particularly to a wall-mounted, racklike device for disinfecting and storing elongated medical instruments such as endoscopes and the like.

With particular reference to endoscopy, after each use of an endoscope it is a common practice to coil up the flexible, elongated insertion tube portion thereof and place it in its coiled condition into a bucketlike basin containing, for example, up to a gallon or more of relatively expensive disinfecting liquid such as glutaraldehyde solution. After a predetermined soak time period, the insertion tube portion is removed from the basin, uncoiled, and, then rinsed with water to remove disinfecting liquid therefrom. This prior art endoscope disinfecting procedure is disadvantageous for two primary reasons.

Firstly, the flexible insertion tube portion of the endoscope typically contains a relatively fragile, elongated, fiber optic bundle that can be damaged by repeated coiling and uncoiling of the insertion tube such as during routine disinfecting procedures as noted above. Major endoscope manufacturers recommend that, to the extent possible, the endoscope insertion tube should be maintained in an uncoiled, straightened condition when not in use, i.e. when being cleaned, disinfected, or stored.

Secondly, it is believed that the above-noted prior art disinfecting technique uses far more disinfecting liquid than is required to adequately disinfect an endoscope insertion tube. Thus, expensive disinfecting liquid is wasted resulting in significant cost ineffectiveness.

There is a need for a durable, low cost device that economically disinfects and efficiently stores one or more endoscopes in an uncoiled, straightened condition.

SUMMARY OF THE INVENTION

In accordance with the present invention, at least one elongated, generally vertically extending tube holds disinfecting liquid. The insertion portion of the endoscope is received into an open top end of the tube, and is completely immersed in and wetted by the disinfecting liquid. Preferably the tube is of circular cross section and is formed of extruded polyvinyl chloride plastic that is transparent to permit visual inspection of the endoscope insertion portion and of the level of disinfecting liquid in the tube during a disinfecting cycle. The transparency of the tube also allows the user to check the liquid contained therein for contamination.

Means are provided for closing the bottom end of the vertically extending tube to preclude leakage of disinfecting liquid therefrom. The preferred form of such closing means is an elastomeric plug that is press-fitted into the bottom end of the tube in fluidtight relation therewith. Alternatively, a user-actuated valve can be provided to close the bottom end of the tube, the valve being operable to open such tube bottom end to permit drainage of the disinfecting liquid from the tube via the valve.

In further accordance with the invention, means are also provided for mounting the tube to a vertical surface such as a wall. The mounting means preferably includes top and bottom, vertically spaced, wall-mounted brackets interconnected by elongated rodlike members that support and maintain the brackets in fixed position relative to each other. The tube is positioned between the brackets, and has its bottom end supported by and resting on the bottom bracket. The top end of the tube engages locking means which hold the tube in position. The locking means is releaseable to allow the tube to be removed from between the brackets for cleaning at a remote location. Preferably, the locking means is constituted by an annular cam-action nut that is rotatably received in an aperture in the top bracket. When rotated in one direction, the nut moves downwardly to apply a compressive force to the top end of the tube thereby pushing its bottom end against the lower bracket to in effect lock the tube in position between the brackets. When rotated in the other direction, the nut moves upwardly to release the tube for removal from its normal mounted position between the brackets.

In addition to the above features, the present invention provides visual level indicator means to assist in refilling the tube to a desired level with disinfecting liquid subsequent to a disinfecting liquid changeover or tube cleaning operation. With particular regard to tube cleaning, at least one of the rodlike members interconnecting the brackets is removable for use as a cleaning rod for swabbing out the tube to clean its interior wall.

BRIEF DESCRIPTION OF THE DRAWINGS

A fuller understanding of the invention may be had by referring to the following description and claims taken in conjunction with the accompanying drawings, wherein:

FIG. 3 is a front elevation view of a shelflike top bracket constituting a component of the present invention;

FIG. 4 is a top plan view of the bracket of FIG. 3;

FIG. 5 is a front elevation view of a shelflike bottom bracket constituting a component of the present invention;

FIG. 6 is a top plan view of the bracket of FIG. 5;

DETAILED DESCRIPTION OF THE PREFERRED EMBODIMENTS

Figure 1:
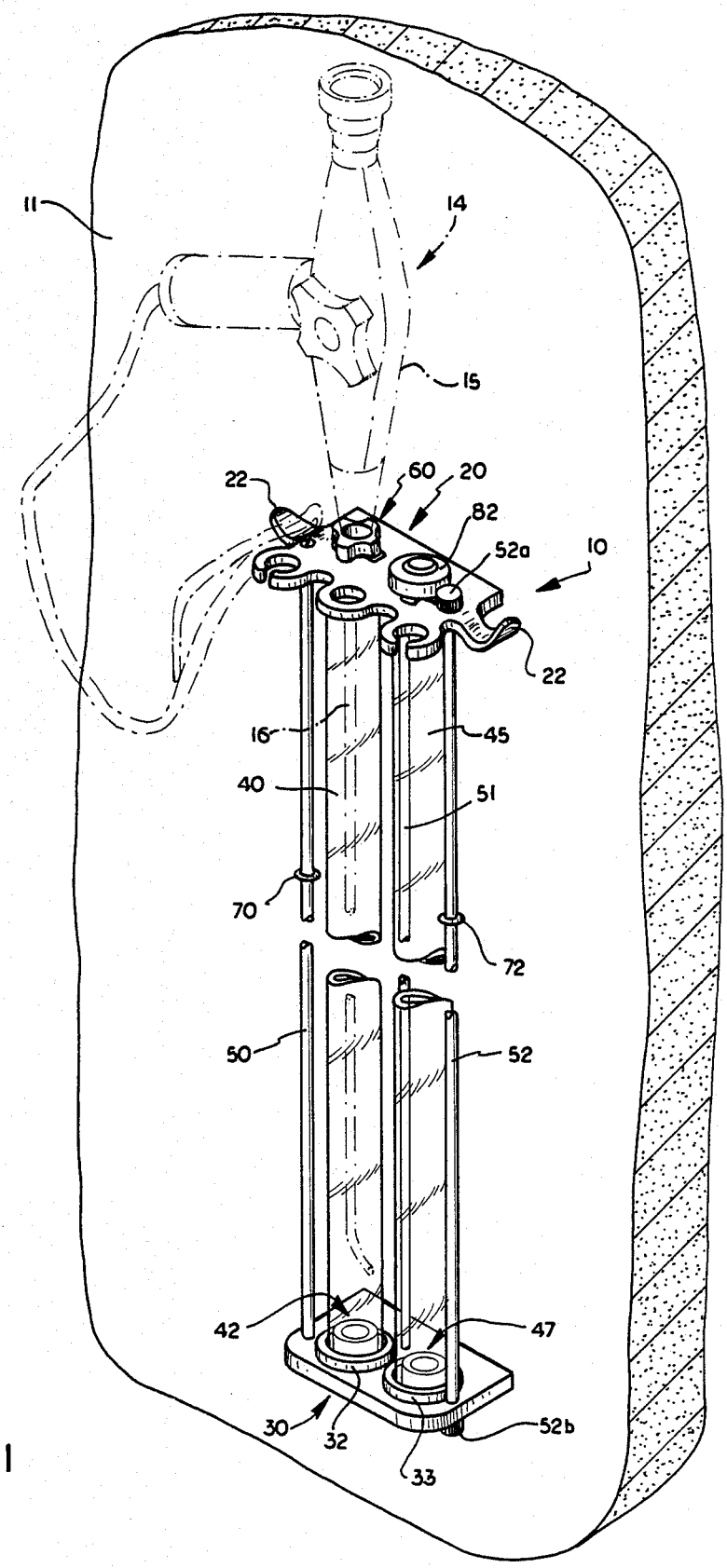
FIG. 1 is a perspective view of a wall-mounted, racklike, endoscope disinfecting and storage device in accordance with the present invention with its middle portion cut away.
Figure 2:
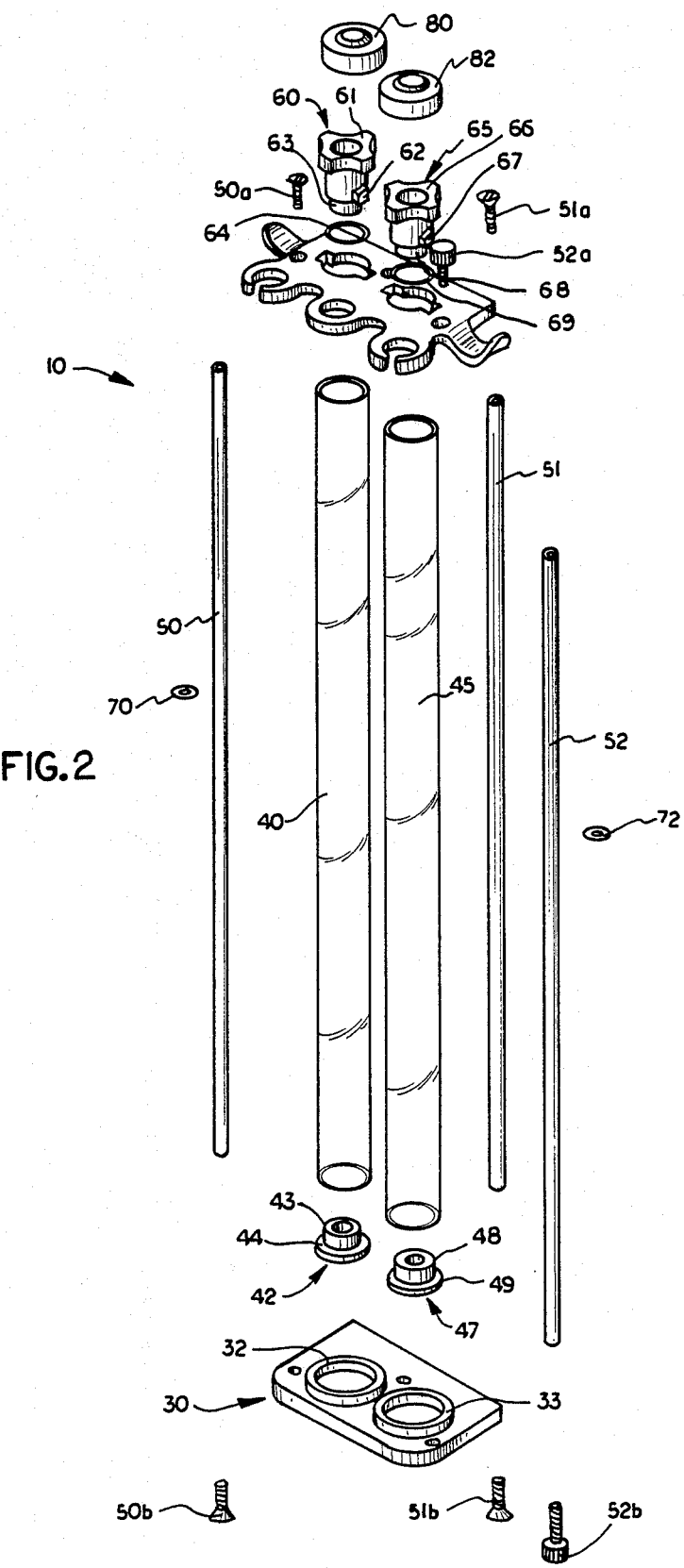
FIG. 2 is an exploded view of the device illustrated in FIG. 1 with no portions cut away.

In accordance with the present invention and with particular reference to FIGS. 1 and 2, a racklike device 10 for disinfecting and storing elongated medical instruments such as endoscopes and the like is illustrated. In FIG. 1, the device 10 is shown in its normal position for use by being mounted to a support surface lying in a generally vertical plane such as a wall 11. In FIG. 2, the device 10 of FIG. 1 is shown with its components separated from each other in a disassembled condition to provide a clearer, more complete view of such components.

It is to be noted that while the following discussion will be directed primarily to endoscopes (bronchoscopes, gastroscopes, colonoscopes, etc.) it is clearly contemplated that the device 10 may find use in the disinfecting and storing of other elongated medical instruments, especially those of a flexible type, such as endoscopy forceps, as will become apparent. It is also to be noted that the device 10 is intended for maintaining medical instruments used in both the veterinary and human medicine fields.

The device 10 includes a pair of vertically spaced, wall-mounted bracket means in the form of a shelflike top bracket 20 and a shelflike bottom bracket 30, the brackets being in the form of aluminum alloy castings for example, and being interconnected by a plurality of elongated rodlike members for supporting and maintaining the brackets in fixed, spaced apart position relative to each other. Such interconnecting members are illustrated in the preferred form of a left connecting rod 50, a middle connecting rod 51 and a right connecting rod 52. The ends of each of the rods 50, 51, 52, all having circular cross sections and of equal lengths, are provided with threaded blind bores for receiving fastening means such as plated or stainless steel screw members which extend through apertures in the top and bottom brackets 20, 30, wherein the top bracket 20 is fixed to the top ends of the three connecting rods 50, 51, 52, while the bottom bracket 30 is fixed to the bottom ends of the three connecting rods 50, 51, 52.

The elongated rods 50, 51, 52 extend vertically in generally parallel relation to each other between the brackets 20, 30, the left and right rods 50, 52 being positioned toward the front corners of the main portions of the shelflike brackets 20, 30, with the middle rod 51 being located toward the rear of the brackets 20, 30, and being horizontally centered along the rear edge of said brackets so that in a plan view, the rods 50, 51, 52 form a triangular pattern. The rods can, for example, be formed of plated steel or of anodized aluminum.

Also extending between the brackets 20, 30 are elongated generally vertically extending tube means in illustrated form of a left soaking tube 40 and a right soaking tube 45, the tubes being parallel to each other and the rods 50, 51, 52, and being spaced apart a slight distance as illustrated. The tubes 40, 45 are formed, for example, of extruded polyvinyl chloride plastic that is transparent to permit visual inspection of the tube interiors.

Means for closing the bottom ends of the tubes 40, 45 are preferably comprised by a left tube elastomeric plug 42 and a right tube elastomeric plug 47, the rubberlike plugs 42, 47 being press-fitted in fluidtight relation into the bottom ends of the tubes 40, 45 in a manner to be subsequently illustrated in greater detail.

While two tubes 40, 45 are illustrated in the preferred embodiment, it is clearly contemplated that a single tube version of the device 10, or a version having more than two tubes, could be provided in accordance with the present invention, the number of tubes depending on the number of endoscopes or the like desired to be disinfected and stored in the device 10 as will be apparent to those skilled in the art. It is also to be noted that the term "disinfected" as used herein is also intended to encompass "sterilizing", it being recognized that sterilizing of a medical instrument will result from a longer soak time in a disinfecting liquid such as glutaraldehyde solution as is well known in the art.

With particular reference to FIG. 1, an endoscope 14 (shown in phantom) of a typical type can be seen to include a control unit 15, and an elongated flexible insertion tube portion 16 that has been inserted into the open top end of the left tube 40 via an annular member in the preferred form of a left tube lock nut 60 which constitutes a releaseable locking means to maintain the left tube 40 in position between the brackets 20, 30 as will be discussed in greater detail. It can be seen that the lower end of the control unit 15 of the endoscope 14 rests on the left tube lock nut 60, which in turn is supported by the top bracket 20, the endoscope insertion portion 16 hanging downwardly into the interior of tube 40 which contains disinfecting liquid such as a glutaraldehyde solution as noted earlier. The top bracket 20 includes a pair of hooklike projections 22 over which can be hung for example a cablelike light guide forming a part of the control unit 14 as illustrated.

With further reference to FIG. 1, the right tube 45 is not in use, and therefore its top end is covered by the cap 82, formed of vinyl plastic material, which precludes foreign matter from falling into the tube 45, and also inhibits evaporation of liquid contained therein. It will be recognized that a second endoscope could simultaneously be disinfected with endoscope 14 by utilization of tubes 45 wherein cap 82 would be removed as has been a left tube cap 80 (see FIG. 2) used to close the top end of tube 40 when not in use.

The left tube 40 preferably is of a circular cross section and extends substantially linearly so that it advantageously maintains the elongated portion 16 of the endoscope 14 in a generally straightened condition when contained in the tube and immersed in the disinfecting liquid during a disinfecting or sterilizing cycle. Thus, coiling of the flexible endoscope portion 16 is avoided to preclude the possiblity of damaging the fiber optic bundle contained therein. Also, all surfaces of the straightened portion 16 of the endoscope 14 are exposed to and more easily wetted by the disinfecting liquid as compared to the earlier discussed prior art disinfecting technique wherein the portion 16 may be coiled upon itself in contiguous relationship.

In further accordance with the present invention, visual level indicator means are provided to indicate a desired level of disinfecting liquid in tubes 40, 45 that is to be maintained when no endoscope portions are inserted therein to ensure proper disinfecting as will become apparent. Since the tubes 40, 45 are formed from transparent plastic, the actual liquid level in the tubes 40, 45 can be easily checked relative to a desired liquid level as indicated by the position of the visual level indicator means that will now be discussed. Preferably, such visual level indicator means are in the form of a left elastomeric O-ring 70 slidably mounted on the left connecting rod 50, and a right elastomeric O-ring 72 slidably mounted on the right connecting rod 52, the rods 50, 52 being parallel and adjacent to their respective tubes 40, 45 as illustrated. The O-rings 70, 72 frictionally engage the circular cross section rods 50, 52 but are slidable up and down thereon so that they can serve to indicate a desired level of disinfecting liquid in the associated tube.

As will be recognized by those in the art, the endoscope insertion portion 16, when placed into tube 40 will displace a predetermined amount of disinfecting liquid contained therein wherein the level of liquid in the tube will rise. It is important that only the proper amount of disinfecting liquid be contained in the tube 40 so that disinfecting liquid will not overflow out of the top of the annular lock nut 60 when the endoscope portion 16 is fully inserted into the tube for disinfecting. Thus, by mathematical calculation, or by trial and error, the O-ring is slid to mark the desired level of liquid in the adjacent tube 40 when no endoscope portion is contained therein so that upon insertion of the endoscope portion 16 into the tube 40 the level of liquid will rise to the top of such portion 16 but will not rise so as to overflow out of the tube 40 via lock nut 60. Thus, it can be seen that a very simple means is provided for indicating the desired level of liquid in the tubes 40, 45 that should be maintained to insure proper disinfecting of endoscope portions inserted therein without spillage of disinfecting liquid. As will also be discussed in greater detail, the tubes 40, 45 are removable from their positions between the brackets 20, 30 to a remote location for liquid changeover or cleaning so that when the now empty tubes are returned to their position as illustrated in FIG. 1 they can easily be refilled with disinfecting liquid to the desired level indicated by the O-rings 70, 72, the vertical positions of the O-rings 70, 72 being different where two different sized endoscopes are simultaneously disinfecting in their respective tubes 40, 45.

In accordance with another feature of the present invention, top and bottom knurled screws 52a, 52b are provided for fastening rod 52 to brackets 20, 30 and can be gripped by a user and easily unscrewed so that rod 52 can be removed from between the bracekts 20, 30 for use as a cleaning rod for swabbing out, with appropriate swabbing material, the tubes 40, 45 so as to clean their interior walls. The rod 52 can also be used to push out from the interiors of tubes 40, 45 the plugs 42, 47.

With particular reference to FIGS. 3 and 4, the top bracket 20 can be seen to include the earlier noted pair of hooks 22 each extending from one end (left or right) of the bracket 20 as illustrated. The bracket 20 includes a top side 20a, and a bottom side 20b from which downwardly extend, along its back edge, a pair of horizontally spaced wall-engaging mounting tabs 21 each having an aperture 21a for receiving appropriate fastening means such as a screw for fastening the bracket 20 to a wall wherein the bracket's major portion extends horizontally outwardly therefrom in shelflike fashion as illustrated in earlier discussed FIG. 1.

With particular reference to FIG. 4 and FIG. 2, the top bracket 20 includes a left tube lock nut aperture 23 for releasably and rotatably retaining the earlier discussed left tube lock nut 60, and further includes a right tube lock nut aperture 24 for releasably and rotatably retaining a right tube lock nut 65 identical to the left tube lock nut 60, the nuts 60, 65 preferably being constituted by, for example, anodized aluminum alloy castings. With particular reference to FIG. 2, it can be seen that the tube lock nuts 60, 65 are annular in cross section and include grippable upper ends 61, 66. Slightly below their midportions the nuts 60, 65 include cam means in the preferred form of diametrically opposed cam ramp portions 62, 67 (only one projection on each nut shown in FIG. 2). The nuts 60, 65 also include reduced diameter lower ends 63, 68 which are engageable with respective top ends of the tubes 40, 45 and apply thereto a compressive force pushing the tubes 40, 45 downwardly against the lower bracket 30 as will be subsequently discussed and illustrated in greater detail.

Thus, the annular nuts 60, 66 are generally cylindrical in shape but for the radially extending, diametrically opposed, cam ramp projections 62, 67 which, with reference to FIG. 4 are received and pass through in opposed slot portions 23a, 24a. Thus, the nuts 60, 65 are inserted downwardly into the apertures 23, 24 and can be rotatably retained therein as long as the cam projection 62, 67 are not vertically aligned with the slot portions 23a, 24a of the apertures 23, 24. As will become apparent, when the nuts 60, 65 are rotated on the elongated axis on which the tubes 40, 45 lie, the cam ramp projections 62, 67 will engage a circular cam track portion on the underside 20b of the bracket 20 and will cause the nuts 60, 65 to move to and away from the lower bracket 30 wherein the tubes 40, 45 are either locked in position between the brackets 20, 30 or are removable therefrom when the lock nuts 60, 65 are lifted up out of the apertures 23, 24. Thus, the nuts 60, 65 in conjunction with the apertures 23, 24 and cam track portions of the bracket underside 20b function as releasable locking means for mounting the tubes 40, 45.

With particular reference to FIG. 4, it can be seen that a left side endoscope hanging aperture 25 and a right side endoscope hanging aperture 27 are also provided at the front end of the top bracket 20. The apertures 25, 27 have open front ends which will accept the thickness of the endoscope insertion portions (e.g. portion 16, see FIG. 1) so that such portions can be laterally moved into the apertures 25, 27 wherein the endoscope is supported by the top bracket with the portions 16 hanging downwardly therefrom in a straightened condition outside of the associated tubes 40, 45. It is also contemplated that while the tubes 40, 45 normally contain disinfecting liquid, they could also contain other liquid, such as rinse water, or could be used in an empty condition for protected storage of the endoscope insertion portion 16.

With further reference to FIG. 4, the top bracket 20 also provides an aperture 26 for receiving and supporting a typical aspiration syringe associated with the normal cleaning of endoscopes as is well recognized in the art. Finally, the top bracket 20 includes smooth bore apertures 50a', 51a' and 52a' which (see FIG. 2) receive screw members 50a, 51a and 52a which are threaded into the top ends of the rods 50, 51, 52 as noted earlier to fixedly attach the bracket 20 to such top ends of the rods.

With reference to FIGS. 5 and 6, the bottom bracket 30 is more clearly illustrated as including a top side 30a, and a bottom side 30b from which downwardly extends from the back edge thereof in horizontally spaced relation a pair of wall engaging mounting tabs 31 each having an aperture 31a for receiving a suitable fastening means, e.g. screws, for mounting the bottom bracket 30 to a wall wherein, like the top bracket 20 discussed earlier, a major portion of the bottom bracket 30 will horizontally extend outwardly from the wall in shelflike fashion as illustrated most clearly in FIG. 1. With particular reference to FIG. 6, the bottom bracket includes a plurality of smooth bore apertures 50b', 51b', 52b' for receiving (see FIG. 2) a plurality of screw members 50b, 51b, 52b which thread into the bottom ends of the rods 50, 51, 52 to fixedly attach the bracket 30 to the bottom ends of such rods. With further reference to FIGS. 5 and 6, the bottom bracket also provides a circular, upraised, left tube retaining lip 32, and a circular, upraised, right tube retaining lip 33 is illustrated. The circular lips 32, 33 have an interior diameter properly sized for accepting the bottom ends of the tubes 40, 45 (see FIGS. 1 and 2).

Figure 7:
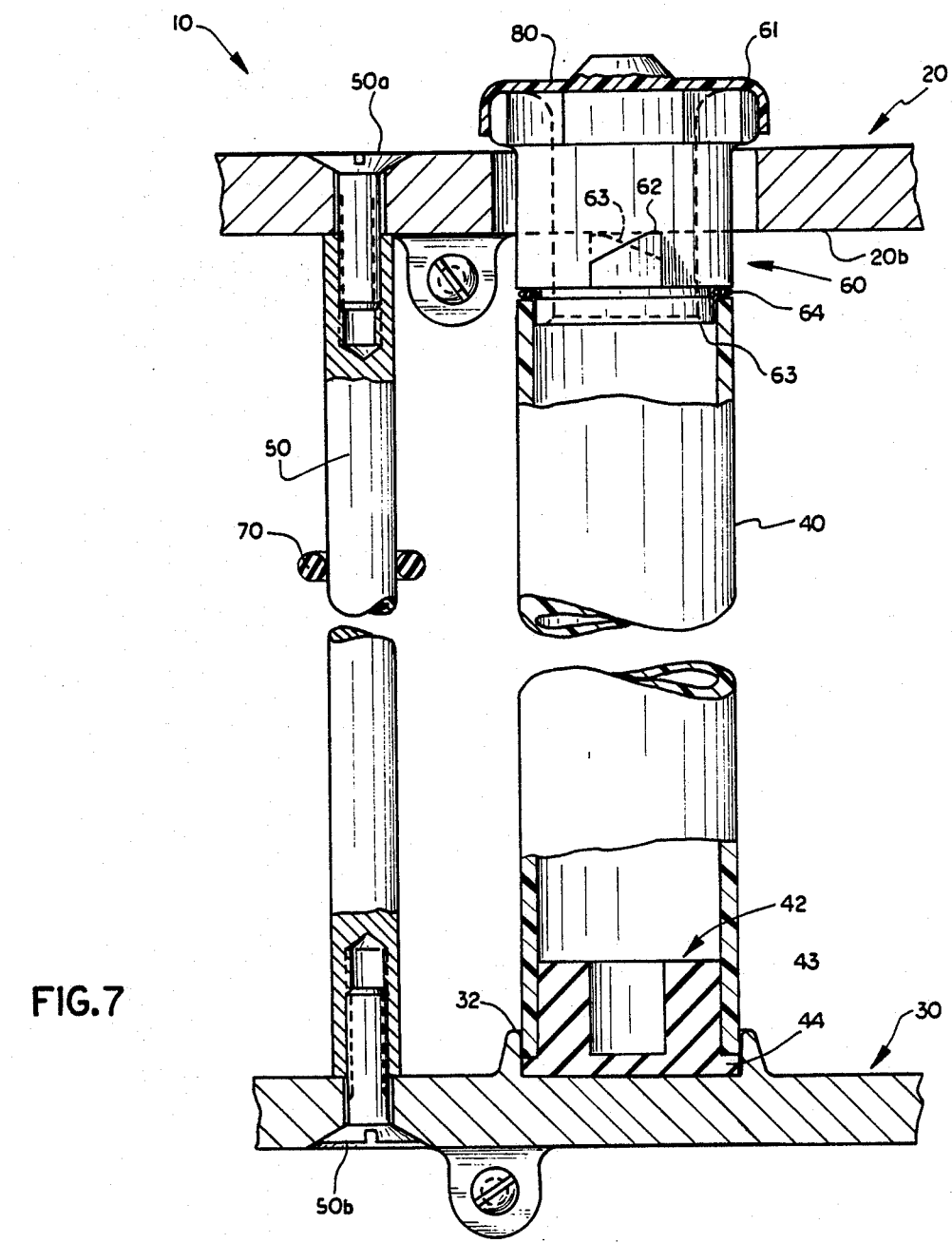
FIG. 7 is an enlarged front elevation view of the left side of the device of FIG. 1 in accordance with the invention with portions cut away.

With reference to FIG. 7, wherein only the left half of the device 10 of FIG. 1 is illustrated, it being recognized at the right half would be similar in construction, the top plate 20 and the bottom plate 30 are held in fixed spaced apart relation by the rod 50 carrying level indicating O-ring 70, the rod 50 having its top end fixed to top bracket 20 by screw member 50a and its bottom end fixed to the bottom bracket 30 by screw member 50b. The circular, upraised, left tube retaining lip 32 provides a circular recess which receives the bottom end of the tube 40 which is closed by the elastomeric plug 42. The plug 42 has an upper reduced diameter portion 43 press-fitted into the bottom end of the tube 40 as illustrated, and a larger diameter lower sealing flange 44 which is interposed between the floor of the recess provided by lip 32 and the end face of the bottom end of the tube 40 so that the flange 44 is normally compressed by the downward force applied to the tube 40 when the tube lock nut 60 is rotated so that the diametrically opposed cam ramp projections 62 (one shown in phantom) engages the underside 20b the bracket 20. Thus, the upper, tube-inserted portion 43 of the plug 42 provides a circular sealing face engaging the interior wall of the tube 40, while the lower sealing flange 44 of the plug 42 provides a face seal. This double sealing action insures that leakage of disinfecting liquid from the bottom end of tube 40 does not occur. With reference to the upper end of the tube 40 it can also be seen that an elastomeric type O-ring 64 is provided about the reduced diameter bottom portion 63 of the lock nut 60. The O-ring 64 engages and is interposed between the top end face of the tube 40 and the nut 60 as illustrated. Thus, when the nut 60 is rotated so that the opposed pair of cam projections 62 are not aligned with the opposed slots 23a (see FIG. 4) the O-ring 64 is compressed to provide a fluid-tight connection between the lock nut 60 and the tube 40.

It can also be seen that the reduced diameter bottom end 63 of the lock nut 60 projects downwardly into the top end of the tube 40 so that when locked in position, the top end of the tube 40 cannot be moved laterally by grasping the top of the tube 40 and attempting to move back and forth. In a similar manner, the lip 32 provided by the bottom bracket 30 also precludes lateral movement of the bottom end of the tube 40 when in its locked position. As will be recognized, when the lock nut 60 is rotated so that it can be lifted up out of its aperture 23 (see FIG. 4) the top end of the tube 40 is free to move outwardly from between the brackets 20, 30 wherein the tubes as a whole can be lifted up out of the recess provided by lip 32 and then removed to a remote location where the disinfected liquid contained therein can be emptied and the plug 42 can be manually removed wherein the connecting member 52 can be used as the cleaning rod to swab out the interior of the tube 40. The plug 42 is then cleaned, appropriately lubricated, and then once again press fitted into the bottom of the tube 40. The tube 40 is replaced in its position wherein the lock nut 60 is inserted downwardly through the top plate 20 and rotated to again, by cam action, move downwardly and lock tube 40 into position. The tube 40 can then be refilled with disinfecting liquid to the desired level indicated by O-ring 70.

As will be recognized by those in the art, the discussion relative to FIG. 7 would also apply to tube 45 (see FIGS. 1 and 2) and its related structures.

Figure 8:
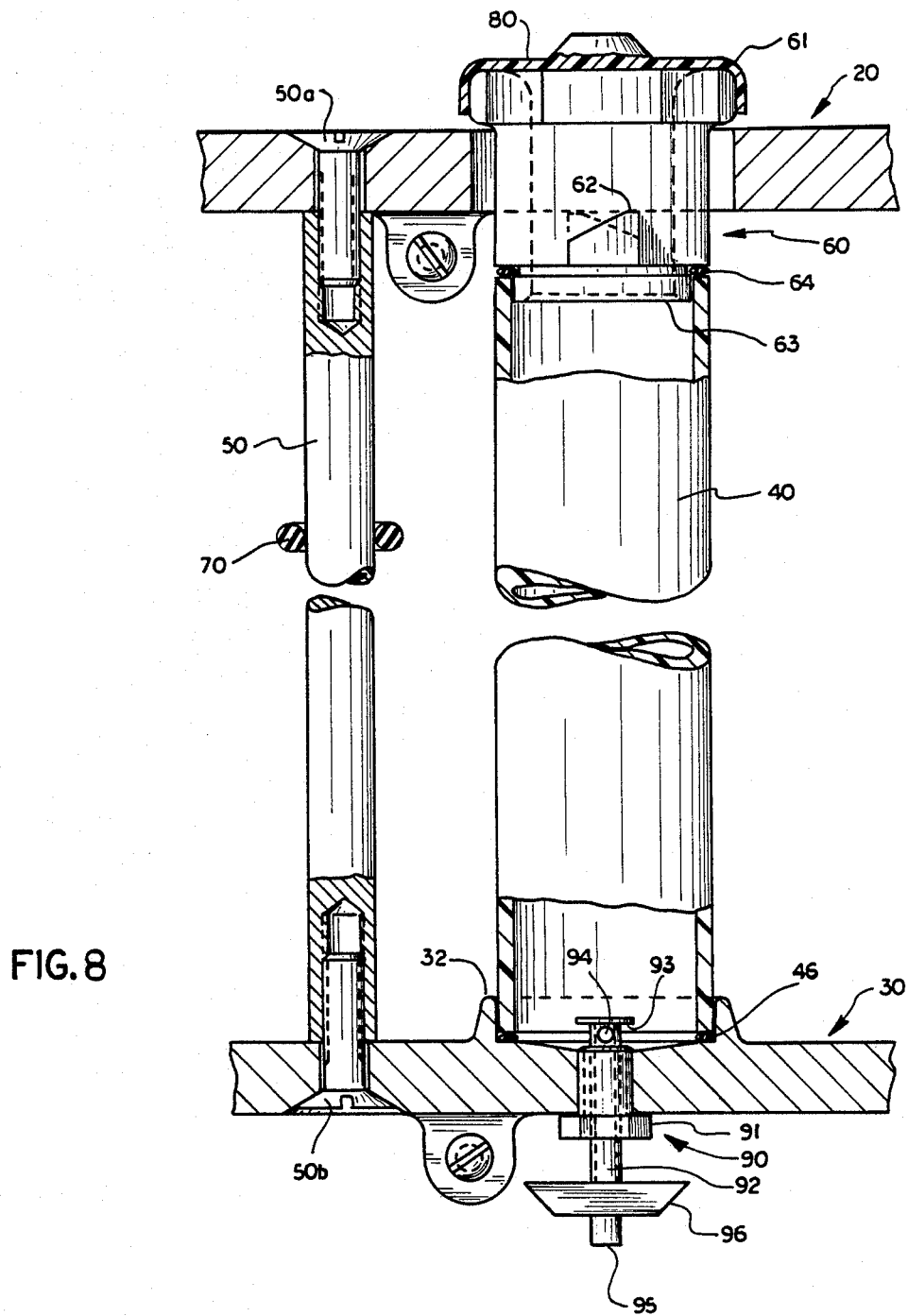
FIG. 8 is an enlarged front elevation view of the left side of a device similar to that of FIG. 1 constituting an alternative embodiment of the invention.

Thus far, the invention embodiment illustrated and discussed requires that the tubes 40, 45 be removed to a remote location to drain liquid therefrom. With reference to FIG. 8, when desired, a conventional valve means 90 can be provided to permit drainage of disinfecting liquid from the tubes 40, 45 when in their mounted positions it being recognized FIG. 8 illustrates only tube 40 with its associated structures, the discussion below also applies to tube 45 and its related structures. The valve means 90 is illustrated in the preferred form of a common plug type valve assembly typically used as a drain means for automobile radiators. The valve means 90 includes a body 91 which is threaded into an aperutre extending through plate 30 along the longitudinal axis of tube 40. The valve body 91 is fixed in position and sealingly engages the aperture in the plate 30, and is annular in shape, the interior cylindrical wall of the valve body 91 being threaded to receive a rotatable hollow shaft 92 carrying at its lower end a spout portion 95 and a manually grippable handle 96. By use of the handle 96, the hollow shaft 92, having a threaded exterior portion engaging the interior of body 91, can be rotated in a clockwise or counterclockwise direction wherein the shaft moves up and down relative to the valve body 91 through which it extends. Fluid communication to the interior of the hollow shaft 92 is provided by a port 94, which in FIG. 7, is shown to be in liquid communication with the interior volume of the tube 40. Thus, the valve means 90 is shown in an open condition wherein liquid will drain from the interior of the tube 40 via the port 94 out of the spout 95 into a drain container of a suitable type. By rotation of the shaft 92, such that it moves downwardly, an annular valve seat face 93 will sealingly engage the top end of the valve body 91 to preclude liquid communication between the port 94 and the interior volume of the tube 40. Thus, it can be seen that, as an alternative to the plug 42 discussed earlier with regard to FIG. 7, the valve assembly 90 can be used where it is desired to have the capability of draining disinfecting liquid without removal of the tubes 40, 45. It should also be noted that with further reference to FIG. 8, that an elastomeric sealing type O-ring 46 is provided to take the place of the earlier discussed lower sealing flange 44 of the plug 42 (see FIG. 7). This O-ring 46 is normally compressed and effectively seals the bottom face of the tube 40 relative to the recess provided by lip 32 of the bottom bracket 30 so that no liquid leakage from the lower end of the tube 40 can occur.

It has been found that a device constructed in accordance with the foregoing description is simple in design, is very rugged, and provides a means for economically disinfecting and efficiently storing endoscopes and the like in a straightened uncoiled condition. Also, it will be recognized that the interior volume of the tube, by proper sizing thereof, will contain only the necessary amount of disinfecting liquid required to effectively disinfect the particular endoscope portion asserted therein.

Although the preferred embodiment of this invention has been shown and described, it should be understood that various modifications and rearrangements of the parts may be resorted to without departing from the scope of the invention as disclosed and claimed herein.

What is claimed is:

1. A device for disinfecting and storing elongated medical instruments such as endoscopes and the like comprising:
    at least one elongated vertically extending tube means for holding disinfecting liquid, the tube means constructed so as to receive at its top end an elongated portion of a medical instrument for immersion in disinfecting liquid;

means for closing the bottom end of the at least one tube means to preclude leakage of disinfecting liquid therefrom, said means for closing comprising a portion held in compression against the bottom end of the at least one tube means to establish a fluid tight compression seal therewith; and means for supporting a medical instrument so that it extends through said top end and for mounting said at least one tube means to a wall-like support surface which lies in a generally vertical plane.

2. A device according to claim 1, wherein said at least one tube means has a generally circular cross section.

3. A device according to claim 1, wherein said portion held in compression against the bottom end of the at least one tube means to establish a fluidtight compression seal is an elastomeric plug having a flange.

4. A device according to claim 1, wherein said at least one tube means extends linearly.

5. A device according to claim 4, wherein the elongated portion of a medical instrument is flexible, said at least one linearly extending tube means maintains the elongated portion of a medical instrument in a straightened condition when contained and immersed in disinfecting liquid in said at least one tube means.

6. A device for disinfecting and storing elongated medical instruments such as endoscopes and the like comprising:

a pair of vertically spaced, wall-mounted brackets, a plurality of elongated members interconnecting said brackets, said interconnecting members supporting and maintaining the brackets in fixed spaced apart positions relative to each other;

at least one elongated, linear tube for containing disinfecting liquid into which an elongated portion of a medical instrument can be inserted and immersed, the at least one tube extending vertically between the brackets;

means for removably connecting at least one of said plurality of elongated members between said brackets so as to use said at least one of said plurality of elongated members as to cleaning rod for swabbing out said at least one tube to clean its interior wall;

means for closing the bottom end of the at least one tube to preclude leakage of disinfecting liquid therefrom; and means for locking the at least one tube in position between said brackets, said locking means being releasable to permit removal of said at least one tube from its position between said brackets for cleaning of said at least one tube at a remote location.

7. A device according to claim 6, wherein said brackets comprises a bottom bracket on which the bottom end of said at least one tube rests for support, and a top bracket for supporting said locking means, said locking means engaging and supporting the top end of said at least one tube.

8. A device according to claim 7, wherein said locking means includes a rotatable annular member carrying cam means, an upper end of the annular member being gripable by a user for rotating of the annular member on a vertical axis along which said at least one tube lies, the lower end of the annular member being engageable with the top end of said tube, said top bracket including an aperture into which said annular member is inserted and releasably retained, said top bracket having adjacent said aperture a cam track engageable with said cam means carried by said annular member wherein rotation on said axis of said annular member in one direction causes the annular member to move toward said bottom bracket, wherein the bottom end of the annular member engaging the top end of the said at least one tube applies a compressive force to the top end of the at least one tube to push said at least one tube bottom end against said bottom bracket, wherein said at least one tube is held in compression and locked in position between the top and bottom brackets, rotation of the annular member in the other direction causing said annular member to move away from said bottom bracket to remove the compressive force from said tube and permit removal of the at least one tube from its position between the said brackets.

* * * * *